(12) United States Patent
Johnston et al.

(10) Patent No.: US 9,119,008 B2
(45) Date of Patent: Aug. 25, 2015

(54) HEARING PROSTHESIS ECHO LOCATION

(71) Applicants: Benjamin Peter Johnston, Wollstonecraft (AU); Frank Risi, Newton (AU)

(72) Inventors: Benjamin Peter Johnston, Wollstonecraft (AU); Frank Risi, Newton (AU)

(73) Assignee: Cochlear Limited, Macquarie University, NSW (AU)

( * ) Notice: Subject to any disclaimer, the term of this patent is extended or adjusted under 35 U.S.C. 154(b) by 175 days.

(21) Appl. No.: 13/965,348

(22) Filed: Aug. 13, 2013

(65) Prior Publication Data
US 2015/0049888 A1    Feb. 19, 2015

(51) Int. Cl.
H04R 25/00    (2006.01)

(52) U.S. Cl.
CPC ............ *H04R 25/505* (2013.01); *H04R 25/606* (2013.01); *H04R 2225/023* (2013.01)

(58) Field of Classification Search
CPC ............ A61N 1/0541; A61N 1/36032; A61B 2019/5251; A61B 2019/5255; A61B 2019/5263; A61B 5/6844; H04R 25/30; H04R 25/60; H04R 25/604; H04R 25/606; H04R 2225/023; H04R 2225/67
See application file for complete search history.

(56) References Cited

U.S. PATENT DOCUMENTS

| | | | |
|---|---|---|---|
| 6,342,035 B1 * | 1/2002 | Kroll et al. | 600/25 |
| 8,099,156 B1 * | 1/2012 | Schnitzer et al. | 600/476 |
| 8,834,545 B2 * | 9/2014 | Stafford et al. | 607/89 |
| 2011/0245714 A1 * | 10/2011 | Volckaerts | 600/559 |
| 2012/0071890 A1 * | 3/2012 | Taylor et al. | 606/129 |
| 2012/0172893 A1 * | 7/2012 | Taylor et al. | 606/130 |
| 2012/0310258 A1 * | 12/2012 | Llinas et al. | 606/130 |
| 2013/0178855 A1 * | 7/2013 | Loquet et al. | 606/80 |
| 2013/0296884 A1 * | 11/2013 | Taylor et al. | 606/130 |

OTHER PUBLICATIONS

Langberg, et al., "The Echo-Transponder Electrode Catheter: A New Method for Mapping the Left Ventricle," JACC, vol. 1, No. 12, Jul. 1988, pp. 218-223.

* cited by examiner

*Primary Examiner* — Matthew Eason
(74) *Attorney, Agent, or Firm* — Edell, Shapiro & Finnan, LLC

(57) ABSTRACT

Presented herein are echo location techniques to obtain information about an implantable component of a hearing prosthesis relative to a recipient's tissue. The hearing prosthesis may comprise an elongate stimulating assembly configured to be implanted in a recipient's where an echo transmitter is disposed in the stimulating assembly. The echo transmitter is configured to emit an energy pulse within the recipient and an echo receiver disposed in the stimulating assembly is configured to detect a portion of the energy pulse reflected from tissue of the recipient.

26 Claims, 9 Drawing Sheets

HEARING PROSTHESIS ECHO LOCATION

BACKGROUND

1. Field of the Invention

The present invention relates generally to hearing prostheses, and more particularly, to hearing prosthesis echo location.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect, a cochlear implant is provided. The cochlear implant comprises an elongate stimulating assembly configured to be implanted in a recipient's cochlea, an echo transmitter disposed in the stimulating assembly configured to emit an energy pulse within the cochlea, and an echo receiver disposed in the stimulating assembly configured to detect a portion of the energy pulse reflected from tissue of the cochlea.

In another aspect, a system is provided. The system comprises a processing device comprising a memory and a processor and an elongate stimulating assembly of a cochlear implant, in communication with echo location processing device, configured to be implanted in a recipient's cochlea. The stimulating assembly comprises an echo transmitter configured to emit an energy pulse, and an echo receiver configured to detect a portion of the energy pulse reflected from the tissue, wherein one or more of the echo transmitter and the echo receiver send echo location signals generated based on the emitted energy pulse and the detected portion of the emitted energy pulse to the processing device.

In another aspect, a method is provided. The method comprises emitting an energy pulse from an echo transmitter disposed in a stimulating assembly positioned in a recipient's cochlea, detecting, within an echo receiver of the echo location device, a portion of the energy pulse reflected from tissue of the recipient, and determining, based at least on the portion of the energy pulse detected at the echo receiver, information about the stimulating assembly relative to the recipient's cochlea.

BRIEF DESCRIPTION OF THE DRAWINGS

Embodiments of the present invention are described herein in conjunction with the accompanying drawings, in which.

DETAILED DESCRIPTION

Embodiments presented herein are generally directed to the use of echo location techniques to obtain information about an implantable component of a hearing prosthesis relative to a recipient's tissue (e.g., osseous, connective (including mineralized), muscle, nervous, and epithelial). For ease of illustration, echo location techniques are primarily described herein with reference to a stimulating assembly of a cochlear implant (also commonly referred to as cochlear implant device, cochlear prosthesis, and the like; simply "cochlear implant" herein). However, it is to be appreciated that echo location techniques may be used in conjunction with implantable components of other auditory prostheses (e.g., bone conduction devices, auditory brain stimulators, mechanical stimulators, etc.).

Figure 1:
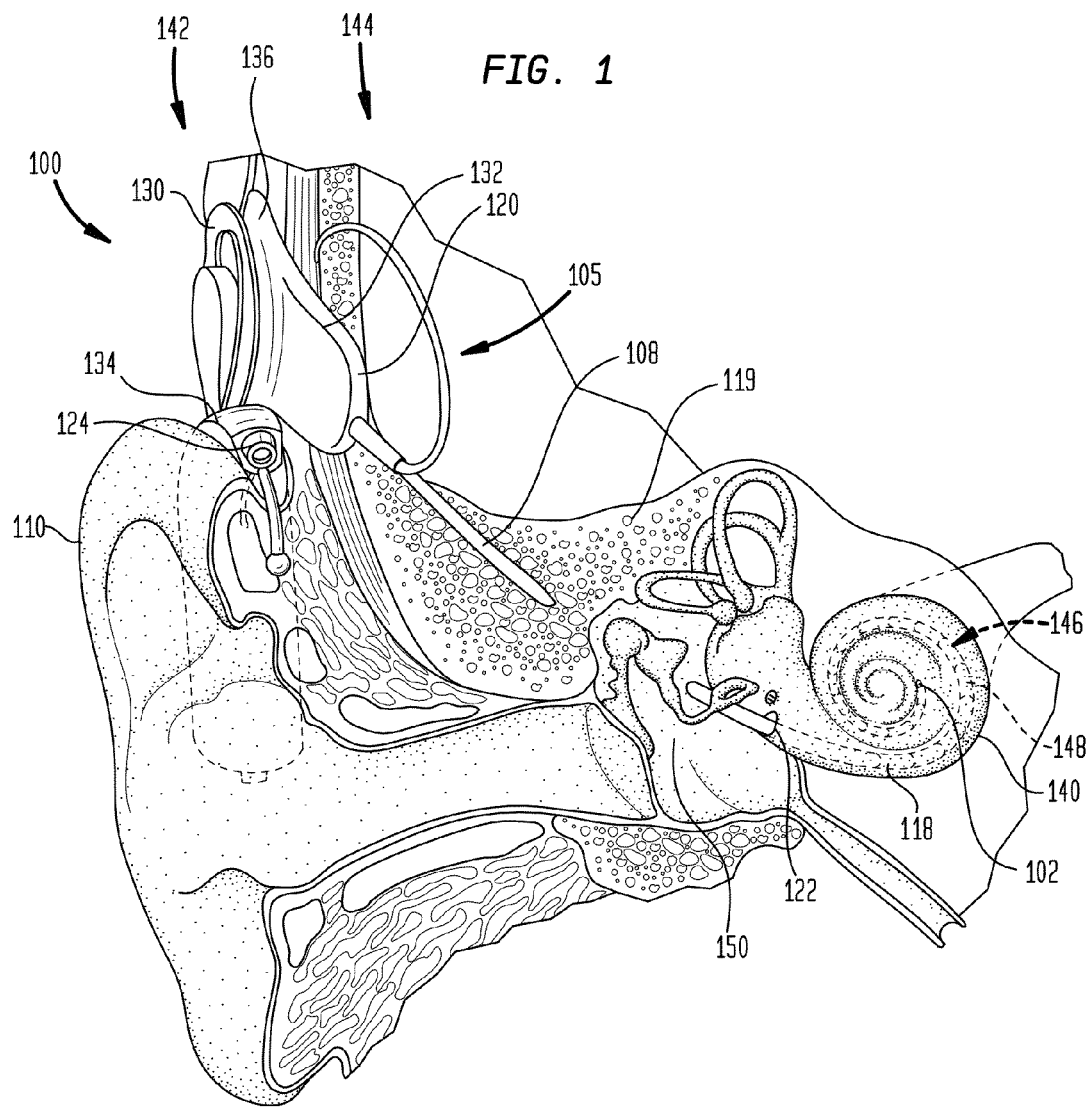
FIG. 1 is a schematic diagram of a cochlear implant configured to implement echo location techniques in accordance with embodiments presented herein.

FIG. 1 is perspective view of an exemplary cochlear implant 100 in accordance with embodiments presented herein. The cochlear implant 100 includes an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), an external coil 130 and, generally, a magnet (not shown) fixed relative to the external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The implantable component 144 comprises an implant body 105, a lead region 108, and an elongate stimulating assembly 118. The implant body 105 comprises a stimulator unit 120, an internal coil 136, and an internal receiver/transceiver unit 132, sometimes referred to herein as transceiver unit 132. The transceiver unit 132 is connected to the internal coil 136 and, generally, a magnet (not shown) fixed relative to the internal coil 136. Internal transceiver unit 132 and stimulator unit 120 are sometimes collectively referred to herein as a stimulator/transceiver unit 120.

The magnets in the external component 142 and implantable component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is implanted in cochlea 140 and includes a contact array 146 comprising a plurality of stimulating contacts 148. Stimulating assembly 118 extends through cochleostomy 122 and has a proximal end connected to stimulator unit 120 via lead region 108 that extends through mastoid bone 119. Lead region 108 couples the stimulating assembly 118 to implant body 105 and, more particularly, stimulator/transceiver unit 120. In the embodiments of FIG. 1, an echo location device 102 is disposed at a first location in the stimulating assembly 118. As described further below, the echo location device 102 is used to obtain information about the stimulating assembly 118 relative to the recipient's cochlea 140.

There are a variety of types of intra-cochlear stimulating assemblies that may be inserted into a recipient's cochlea. For example, a perimodiolar stimulating assembly is a stimulating assembly that is configured to adopt a curved configuration during and/or after implantation into the recipient's cochlea. To achieve this, the stimulating assembly may be pre-curved to the same general curvature of a cochlea. Perimodiolar stimulating assemblies are typically held straight by, for example, a stiffening stylet or sheath which is removed during implantation. Varying material combinations or shape memory materials may also be used so that the stimulating assembly may adopt its curved configuration when in the cochlea.

A stimulating assembly can also be a non-perimodiolar stimulating assembly. A non-perimodiolar stimulating assembly may be a substantially straight assembly, a midscala assembly which assumes a midscale position during or following implantation, or a short assembly implanted into at least a basal region of the cochlea. The stimulating assembly may extend towards the apical end of the cochlea, referred to as the cochlea apex.

To insert any of the above or other intra-cochlear stimulating assemblies, such as stimulating assembly 118, an opening (facial recess) is created through the recipient's mastoid bone 119 to access the recipient's middle ear cavity 150. Using this opening, the surgeon creates an opening (the cochleostomy 122) from the middle ear into the cochlea 140 through, for example, the round window, oval window, the promontory or an apical turn of the cochlea 140. The surgeon then gently pushes the stimulating assembly 118 forward into the cochlea 140 until the stimulating assembly achieves a desired position.

In conventional intra-cochlear stimulating assembly insertion techniques, the surgeon typically operates "blind." That is, due to the nature of the access (through the facial recess and the cochleostomy), the surgeon cannot actually see the stimulating assembly once it passes into the cochlea. Therefore, the only feedback about the state of the stimulating assembly during and immediately after the insertion is tactile feedback (i.e., touch/feel of the surgeon).

Historically, the inability to see the stimulating assembly during insertion has been acceptable as surgeons have been trained to rely upon their experience and skill to detect events that can negatively impact the placement of the stimulating assembly within the cochlea. These events include, for example, tip foldover (i.e., where friction and other forces cause the distal end or tip of the stimulating assembly to get caught on a wall of the cochlea), cochlea perforation (i.e., where the tip of the stimulating assembly perforates a wall of the cochlea causing trauma to structures in the cochlea), and/or deformation (i.e., where the stimulating assembly deforms or buckles at a point along its length).

Figure 2:
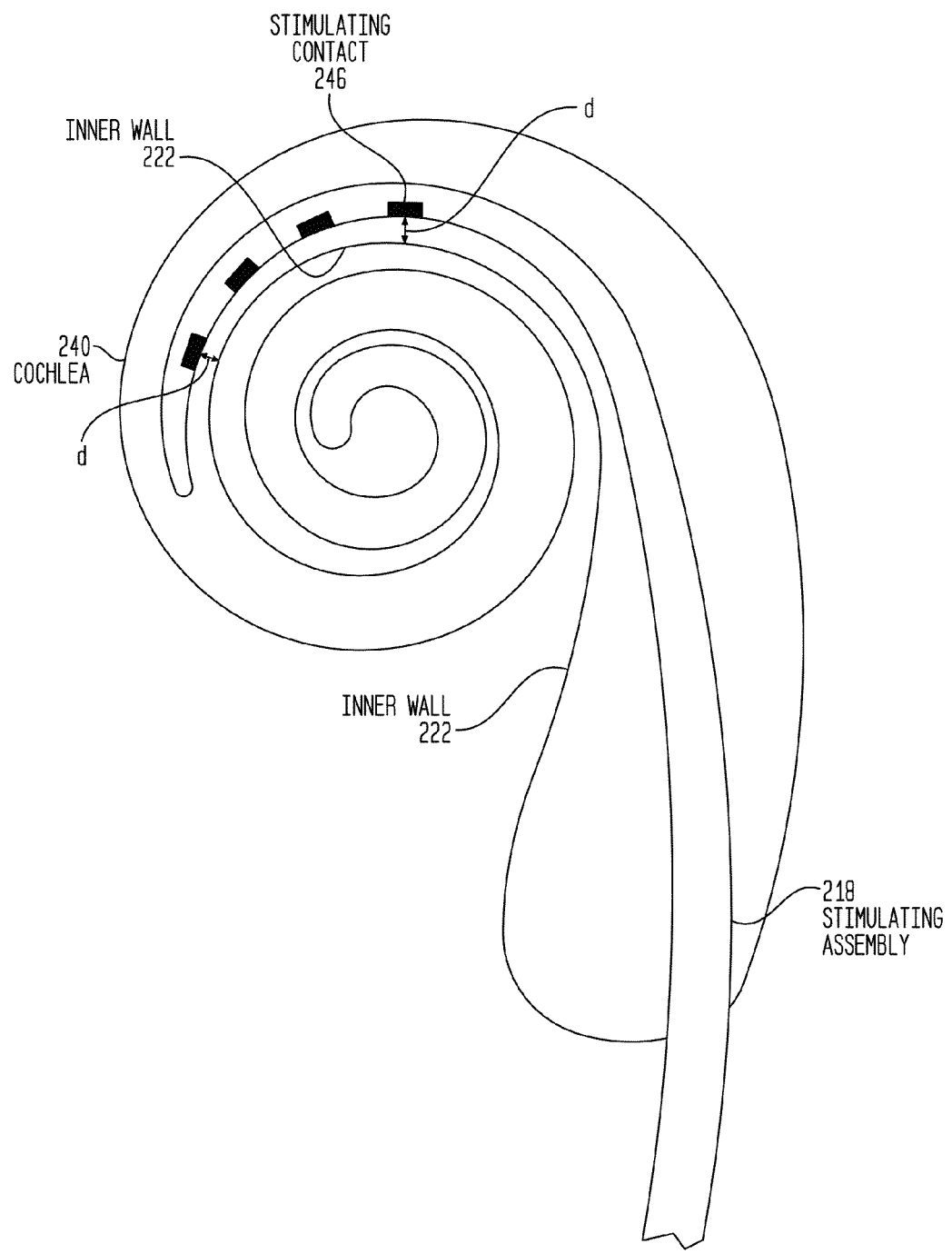
FIG. 2 is a schematic diagram illustrating a mid scalar position of a stimulating assembly within a recipient's cochlea.

More recently, it has been determined that, for at least perimodiolar designs, the proximity of the stimulating contacts to target neural elements (e.g., the modiolus) is positively correlated with cochlear implant performance. That is, performance of a cochlear implant improves when the stimulating contacts are positioned close to the target neural elements. FIG. 2 illustrates an example in which a cochlear implant stimulating assembly 218 has stimulating contacts 246 that, when inserted, are separated from the cochlea inner wall 222 by a distance (d). During insertion, the surgeon attempts to minimize the distance (d) to improve the efficiency of the stimulation provided by stimulating contacts 246.

Although surgeons have become adept at detecting events during insertion (e.g., tip foldover, cochlea perforation, etc.), surgeons may still have difficulty in locating the stimulating assembly at a final position (e.g., close to the target neural elements). This difficulty occurs due to the conventional inability to monitor the insertion path of the stimulating assembly in real time (other than the touch/feel of the surgeon as the surgeon pushes the stimulating assembly into the cochlea). Additionally, the only conventional method for verifying the final position of the stimulating assembly is to complete a post-operative imaging process (e.g., x-ray). However, the need for the stimulating contacts to be in close proximity to the target neural elements has increased, and continues to increase, due to, for example, new stimulating strategies where, as stimulation patterns get more sophisticated, the closeness to the cochlea nerve becomes more desirable. Additionally, stimulating assemblies and stimulating contacts within the assemblies are becoming smaller and smaller. This allows for more precise stimulation of corresponding frequency bands within the cochlea, but also requires more precise positioning of the stimulating contacts and stimulating assembly.

As such, presented herein are echo location techniques that facilitate a controlled and atraumatic insertion of a stimulating assembly into a cochlea with a controlled final position (e.g., a position against or close to the modiolar wall). In general, the echo location techniques presented herein may be used to monitor the state of the stimulating assembly during insertion to look for adverse events (e.g., tip foldover, cochlea perforation, etc.), as well as to monitor the location/position of the stimulating assembly after insertion.

Figure 3:
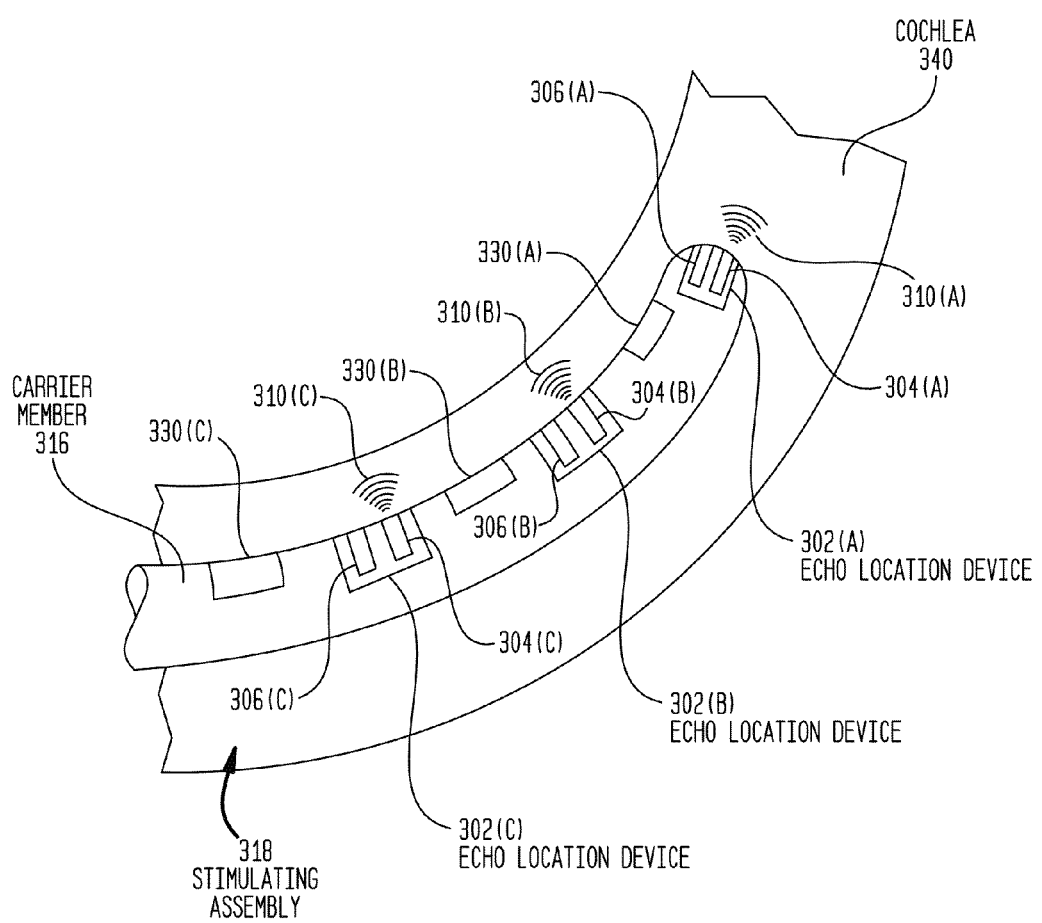
FIG. 3 is schematic diagram of a stimulating assembly in accordance with embodiments of the present invention.

FIG. 3 is a schematic diagram illustrating a portion of a stimulating assembly 318 configured in accordance with the echo location techniques presented herein. The stimulating assembly 318 is shown partially inserted into a recipient's cochlear 340.

Stimulating assembly 318 comprises a carrier member 316 formed from, for example, an elastomer material. Disposed in/on carrier member 316 are three stimulating contacts 330(A), 330(B), and 330(C) In the embodiment of FIG. 3, the stimulating contacts 330(A)-330(C) are electrical contacts, but other embodiments may use other types of contacts (e.g., optical contacts).

The stimulating assembly 318 also comprises a plurality of echo location devices 302(A), 302(B), and 302(C) disposed at various locations within the carrier member 316. The echo location devices 302(A)-302(C) are, in general, configured to provide information to a processing device (not shown) that may be used to determine information about the stimulating assembly relative to the cochlea 340. As described further below, a processing device, using information from the echo location devices 302(A)-302(C), may provide a user (e.g., surgeon, clinician, recipient, caregiver, etc.) with an indication of how close the stimulating assembly 318 is to the walls of the recipient's cochlea. In certain embodiments, the processing device may also or alternatively provide a user with additional information, such as an indication of a speed of insertion of the stimulating assembly 318, depth of insertion, etc.

In the embodiment of FIG. 3, each echo location device 302(A)-302(C) comprises an echo transmitter 304(A)-304(C), respectively, and an echo receiver 306(A)-306(C), respectively. An echo transmitter 304(A)-304(C) and a corresponding echo receiver 306(A)-306(C) are sometimes collectively referred to herein as an echo location pair.

In operation, the echo transmitters 304(A)-304(C) are each configured to emit energy pulses 310(A)-310(C), respectively, within the cochlea 340 and the corresponding echo receivers 306(A)-306(C) listen for echoes (reflections). That is, in certain circumstances, a portion of the energy pulses 310(A)-310(C) emitted by the echo transmitters 304(A)-304(C) will reflect (return) from the walls or other structures of the cochlea 340 (collectively referred to herein as cochlea tissue) back to the associated echo receiver 306(A)-306(C).

The emitted energy pulses 310(A)-310(C) (sometimes referred to as "pings" or "chirps") may be, for example, acoustic energy pulses, electromagnetic energy pulses, optical energy pulses, etc. As such, the use of "echo" or "echo location" should not be interpreted as being limited to the use of acoustic energy pulses. Instead, as used herein, "echo location" generally refers to the generation of information based on the emission of energy signals and the detection of at least a portion of the those signals that reflect from a recipient's tissue, and the subsequent use of that information to generate information about, for example, a stimulating assembly relative to a recipient's cochlea.

In operation, the echo transmitters 304(A)-304(C) are connected to elements (e.g., via wires) that initiate the energy pulses. The echo receivers 306(A)-306(C), and possibly the echo transmitters 304(A)-304(C), are connected to elements that can receive signals generated based on the emitted energy pulses and/or a reflected portion of an energy pulse.

To measure the distance between an echo location device 302(A)-302(C) (i.e., the location at which the echo location device is positioned in the stimulating assembly 318) and cochlea tissue, the time between the transmission of an energy pulse 310(A)-310(C) and the reception of the reflected portion of the energy pulse is measured (determined). This time difference may then be converted into a distance value through calculations that use the speed of the energy (e.g., acoustic, electromagnetic, optical, etc.) within the cochlea 340 (e.g., the cochlea fluid).

In certain embodiments, the Doppler effect can be used to measure the speed (e.g., radial) of the stimulating assembly 318 as it is being implanted and/or how quickly the stimulating assembly is approaching certain features. In such examples, the difference in the frequency of an emitted energy pulse 310(A)-310(C) and a corresponding reflected portion may be measured and converted into a velocity value (i.e., the velocity of the stimulating assembly).

In further embodiments, the cochlea may also elicit a different response to emitted energy pulse 310(A)-310(C) based upon the depth within the cochlea. Using these known/predetermined differences, the depth of insertion of the echo transmitters 304(A)-304(C) (and thus the stimulating assembly 318) may be determined In the embodiment of FIG. 3, the echo location device 302(A) is positioned at the distal end (tip) of the stimulating assembly 318, while the other echo location devices 302(B) and 302(C) are located at various points along the length of the stimulating assembly. As noted above, by measuring the time between the release of an energy pulse 301(A)-310(C) and reception of a reflected portion of the pulse at a the corresponding receiver, the distance between the transmitter and the nearest cochlea tissue (i.e., the tissue that caused the reflection) can be determined. By completing a series of chirp sweeps across all echo location devices 302(A)-302(C) within the stimulating assembly during or after the insertion process, a map of the position of the stimulating assembly relative to the cochlea can be created in real time. One map can be used to determine the position of the stimulating assembly 318 at a given point in time, while several maps can be layered to show the complete trajectory over the insertion process. A sweep across all echo location devices 302(A)-302(C) after the insertion can provide an instantaneous image of the final resting position of the stimulating assembly 318.

As noted above, the energy pulses 310(A)-310(C) may be, for example, acoustic energy pulses, electromagnetic energy pulses, optical energy pulses, etc. In certain embodiments, piezoelectric transducers (e.g., thin film piezoelectric transducers), capacitive ultrasonic transducers, etc. may be used to generate an acoustic energy pulse.

Although FIG. 3 illustrates the use of echo location pairs (i.e., a transmitter with a corresponding receiver), it is to be appreciated that this arrangement is merely illustrative and that other arrangements are possible. For example, in alternative arrangements a single receiver may service (i.e., detect reflections for) multiple transmitters. Additionally, it is to be appreciated that a transmitter and corresponding receiver (i.e., either a receiver specific to the transmitter or a receiver servicing multiple transmitters) may be positioned at different locations within the stimulating assembly. Monostatic operation refers to arrangements in which the transmitter and corresponding receiver are disposed at substantially the same location (e.g., both at the tip of the stimulating assembly), while bistatic operation refers to arrangements in which the transmitter and corresponding receiver are disposed at substantially different locations (e.g., the transmitter disposed at the tip of the stimulating assembly, and the receiver disposed at a mid-point of the stimulating assembly). Multistatic operation refers to arrangements in which more transmitters than receivers (or more receivers than transmitters) are used, again spatially separated. In these various arrangements, the echo location devices may include only an echo receiver, only an echo transmitter, or both an echo receiver and an echo transmitter.

As noted, FIG. 3 has been described with reference to echo location devices that comprise an echo transmitter and an echo transmitter. It is to be appreciated that, in certain embodiments, the echo transmitter and the echo transmitter may be an integrated unit that is sometimes referred to herein as an "echo transceiver" (i.e., a device that performs both transmission and reception operations).

FIG. 3 also illustrates a portion of stimulating assembly 318 that includes three electrical contacts 330(A)-330(C) and three echo location devices 302(A)-302(C). It is to be appreciated that stimulating assemblies in accordance with embodiments presented herein may include different numbers of contacts and echo location devices in different arrangements/orientations. For example, FIG. 4 illustrates an alternative arrangement in which echo location devices are disposed at both the medial and lateral surfaces of a stimulating assembly.

Figure 4:
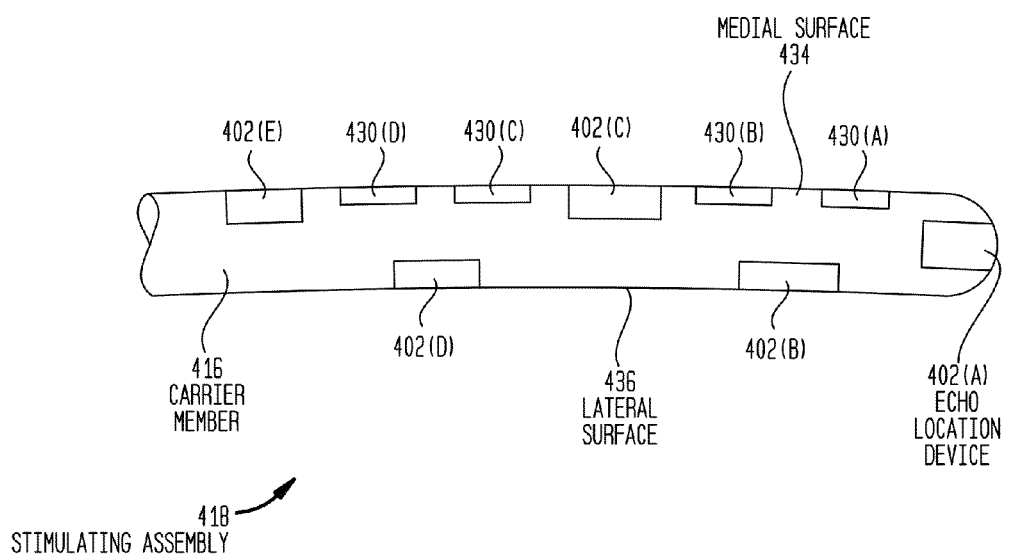
FIG. 4 is schematic diagram of an alternative stimulating assembly in accordance with embodiments of the present invention.

More specifically, FIG. 4 illustrates a portion of a stimulating assembly 418 comprising a carrier member 416. The stimulating assembly 418 includes a medial surface 434 (i.e., a surface configured to be positioned adjacent to the spiral ganglion cells that lie in the bone or modiolus of a recipient's cochlea) and an opposing lateral surface 436 (i.e., a surface configured to face away from the spiral ganglion cells of a recipient's cochlea). The stimulating assembly 418 comprises a plurality of stimulating contacts 430(A)-430(D) disposed along the medial surface 434. The stimulating assembly 418 also comprises a plurality of echo location devices 402(A)-402(E). In this embodiment, echo location device 402(A) is disposed at the distal tip of the stimulating assembly 418, echo location devices 402(C) and 402(E) are disposed at medial surface 434, and echo location devices 402(B) and 402(D) are disposed at lateral surface 436.

It is to be appreciated that arrangements of echo location devices, stimulating contacts, etc. shown in FIGS. 3 and 4 are merely illustrative and that other arrangements are within the scope of embodiments presented herein.

Figure 5:
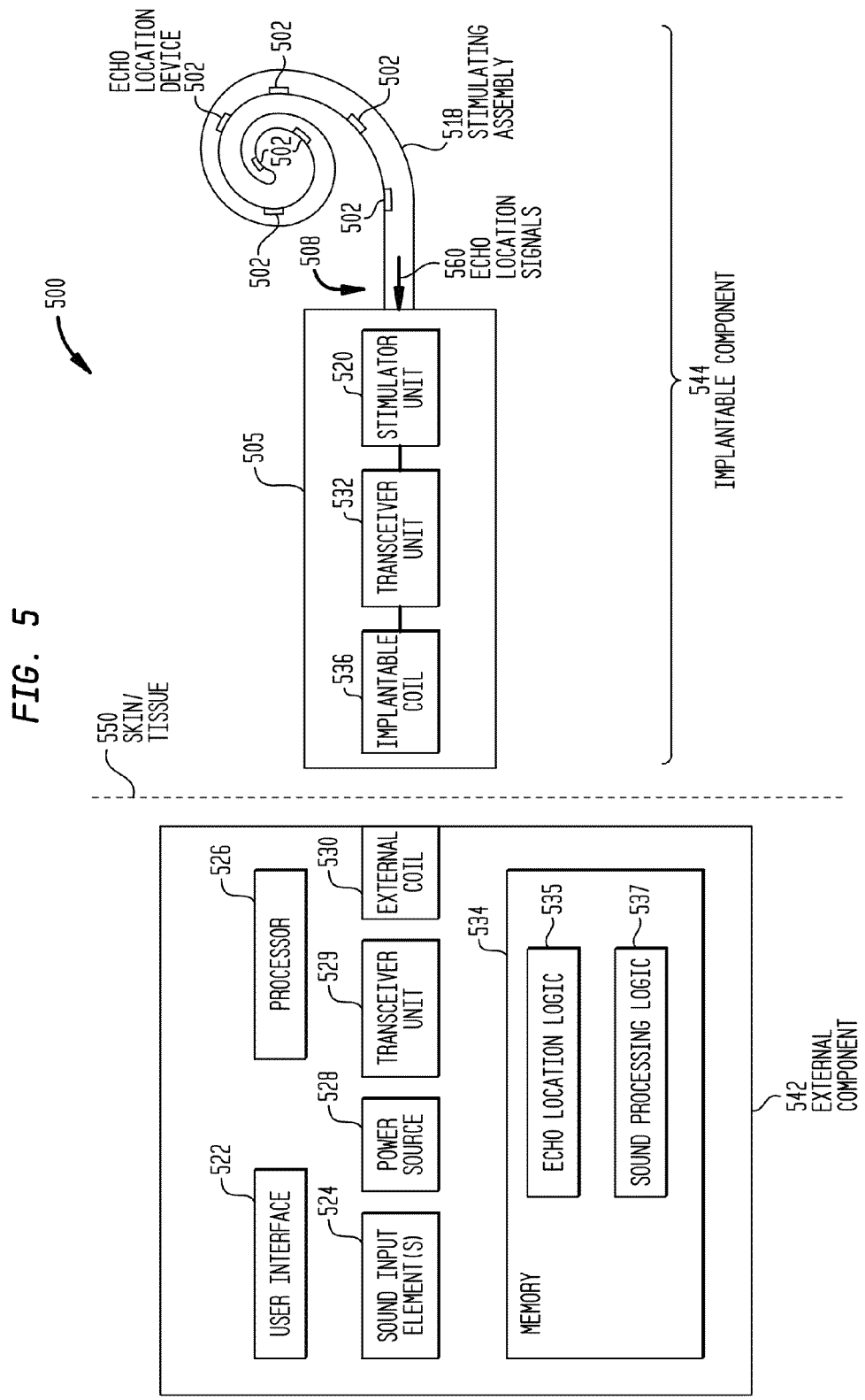
FIG. 5 is a block diagram of a cochlear implant in accordance with embodiments presented herein.
Figure 6:
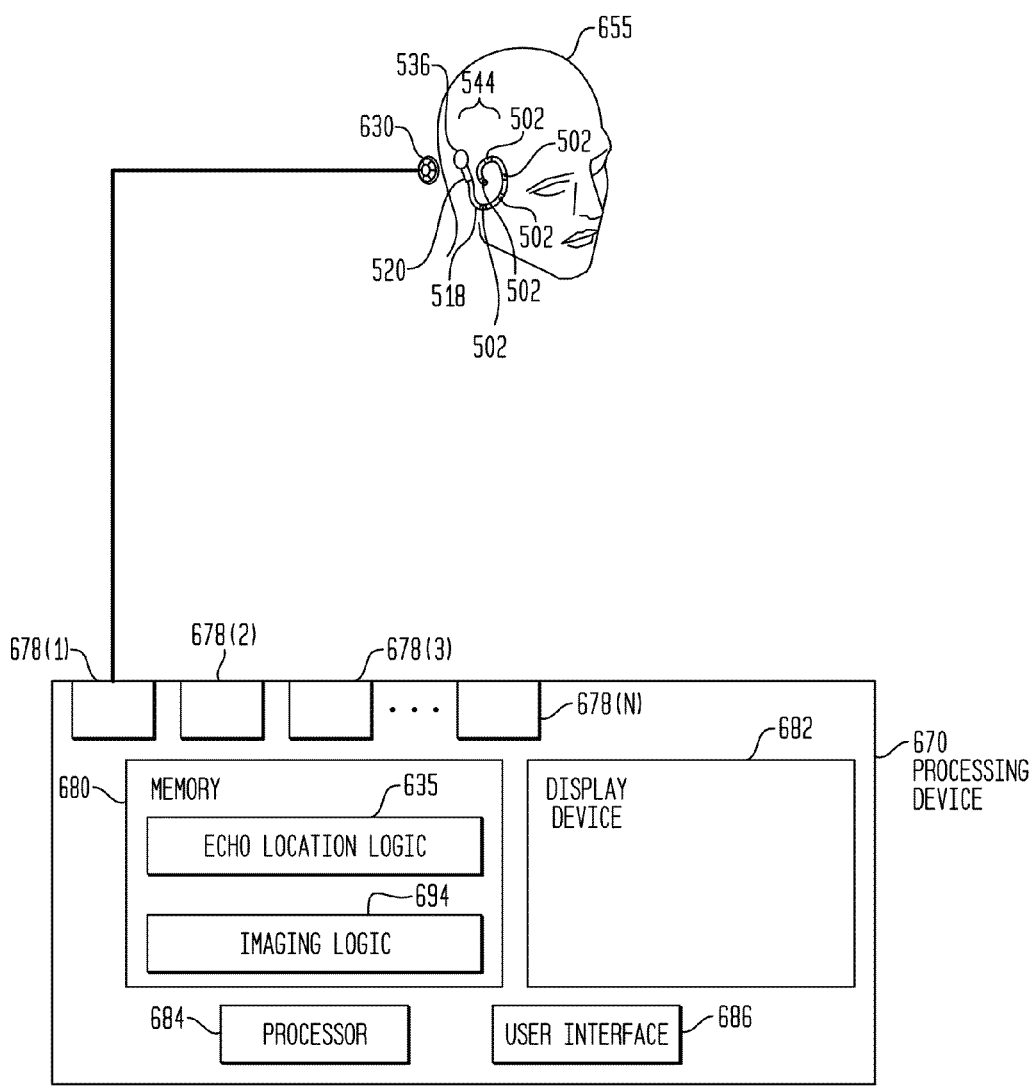
FIG. 6 is a block diagram of an echo location processing device in accordance with embodiments presented herein.

FIG. 5 is a block diagram of a cochlear implant 500 configured for post-operative echo location techniques in accordance with embodiments presented herein. FIG. 6 is a block of a processing device used during implantation echo location techniques accordance with embodiments presented herein.

The cochlear 500 of FIG. 5 comprises an external component 542 and an implantable component 544. The external component 442 comprises a user interface 522, one or more sound input elements 524 (e.g., microphones, telecoils, etc.) for detecting sound, a processor 526, a power source 528 (e.g., battery), a transceiver unit 529, an external coil 530, and a memory 534. Memory 534 comprises echo location logic 535 and a sound processing logic 536.

Memory 534 may comprise read only memory (ROM), random access memory (RAM), magnetic disk storage media devices, optical storage media devices, flash memory devices, electrical, optical, or other physical/tangible memory storage devices. The processor 526 is, for example, a microprocessor or microcontroller that executes instructions for the echo logic 535 and sound processing logic 537. Thus, in general, the memory 534 may comprise one or more tangible (non-transitory) computer readable storage media (e.g., a memory device) encoded with software comprising computer executable instructions and when the software is executed (by the processor 526) it is operable to perform the operations described herein in connection with sound processing logic 537 (i.e., sound processing operations described elsewhere herein) and echo location logic 535 (i.e., echo location operations described elsewhere herein).

The implantable component 544 is disposed beneath a recipient's skin/tissue 550 and comprises an implant body 505 connected to an elongate stimulating assembly 518 via a lead region 508. The implant body 105 comprises a stimulator unit 520, a transceiver unit 132, and an internal coil 536. The transceiver unit 532 is configured to receive signals from, or transmit signals to, transceiver unit 529 in external component 542.

Elongate stimulating assembly 518 is implanted in a recipient's cochlea (not shown in FIG. 5) and includes an array of stimulating contacts (also not shown in FIG. 5). In the embodiment of FIG. 5, stimulating assembly 518 also comprises a plurality of echo location devices 502. As described further above, the echo location devices 502 are configured to provide an indication of a distance between the stimulating assembly 518 and tissue of the recipient, an indication of the speed insertion of the stimulating assembly, or other information about the stimulating assembly 518 relative to the cochlea.

The echo location devices 502 comprise an echo transmitter (not shown in FIG. 5) and/or an echo receiver (also not shown in FIG. 5). As noted above, an echo transmitter emits an energy pulse (e.g., acoustic energy pulse, electromagnetic energy pulse, optical energy pulse, etc.) and a corresponding echo receiver detects a reflection of the emitted pulse from the recipient's cochlea tissue. In certain embodiments, an echo receiver is configured to detect the time when a reflected portion of an emitted energy pulse is received by the echo receiver. In other embodiments, an echo receiver is configured to detect the frequency of a reflected portion of an emitted energy pulse that is received by the echo receiver. In further embodiments, an echo receive may detect both the time when a reflected portion of an emitted energy pulse that is received by the echo receiver as well as the frequency of the received reflected portion. It is to be appreciated that detection of frequency and time are illustrative and other information may be detected by a receiver. For example, phase measurements may be used in alternative embodiments.

In other embodiments, an energy pulse may comprise of a mix of different frequencies and system determined what frequencies and/or phases are returned to a receiver. More specifically, certain tissues may absorb and reflect frequencies differently, thus such embodiments could also assist in positioning the stimulating assembly and/or in identifying features within the cochlea (e.g., useful to identify the basilar membrane, or ossification within the cochlea).

In operation, the echo location devices 502 (i.e., echo receivers and/or echo transmitters) are connected to stimulator 520 via one or more wires (not shown). The stimulator unit 520 is configured to drive the echo location transmitters to emit energy pulses. Additionally, the stimulator unit 520 is configured to receive echo location signals 560 from the echo receivers and/or echo transmitters. The echo location signals 560 are signals that may be used to determine, for example, the time difference between the emission of an energy pulse and the reception of the reflected portion of the energy pulse, the frequency difference between an emitted energy pulse and a reflected portion of that energy pulse, etc. It is to be appreciated that the echo location signals 560 may take a number of different forms so as to convey the information from the echo location devices 502. For example, in certain embodiments, the echo location signals 560 may be raw data signals (e.g., signals indicative of one or more of the pulse emission time, reflection reception time, emitted frequency, reflected frequency, etc.).

In the embodiment of FIG. 5, the echo location signals 560 received at the stimulator unit 520 are transmitted to external component 542 for processing. That is, transceiver unit 532 transmits the echo location signals 560 to transceiver unit 529 via implantable coil 536 and external coil 530. Once the echo location signals 560 are received at the external component 542, the signals may be processed by processor 526 executing echo location logic 535. As such, in the embodiment of FIG. 5, the external component 542 is referred to as an echo location processing device.

The processor 526 may execute echo location logic 535 to determine the distance between an echo location device 502 (i.e., the location of the stimulating assembly 518 at which the echo location device is positioned) and the cochlea tissue. More specifically, the processor 526 uses the echo location signals 560 to determine the time difference between when an energy pulse was emitted and when the reflected portion of the energy pulse was received. With this time difference and knowledge of the speed at which the energy pulse (e.g., acoustic, electromagnetic, optical, etc.) travels within the cochlea (e.g., in the cochlea fluid), the processor 526 can determine the distance between the echo location device 502 and the tissue that caused the reflection of the energy pulse to the receiver.

In other embodiments, the processor 526 may execute echo location logic 535 to determine the speed at which the stimulating assembly 518 is inserted and/or the speed at which the stimulating assembly 518 approaches cochlea tissue. More specifically, the processor 526 uses the echo location signals 560 to determine the difference between the frequency of an emitted energy pulse and the frequency of the received reflected portion of that energy pulse. The Doppler Effect can be used to measure the speed of the stimulating assembly 518 and/or how quickly the stimulating assembly is approaching certain features. In other words, the difference in the frequency is converted into a velocity measurement.

In certain embodiments, the echo location signals 560 may be stored in the memory 534 prior to use by the processor 526. The echo location signals 560 may be stored temporarily (e.g., for use during processing) or semi-permanently (i.e., for subsequent export to another device).

FIG. 5 illustrates an embodiment in which the echo location processing device is part of the cochlear implant 500. The external component 500 may be, for example, a behind-the-ear device, body-worn sound processor, button processor, etc. The arrangement of FIG. 5 may be particularly useful to post-operatively monitor the position of the stimulating assembly 518. For example, in certain circumstances a stimulating assembly, such as stimulating assembly 518, may extrude (i.e., withdraw from) a recipient's cochlea. Extrusion may occur for example when the recipient receives trauma to the head. Extrusion of a stimulating assembly may negatively impact hearing performance of the stimulating assembly. As such, in embodiments presented herein a surgeon or other user may, immediately or shortly after implantation of the stimulating assembly, use echo location techniques to determine the initial post-operative position of the stimulating assembly. The echo location techniques may then be subsequently used (e.g., periodically, or after an event such as a head trauma, during clinician visits, etc.) to evaluate the current position of the stimulating assembly relative to initial post-operative position.

If it is determined that the stimulating assembly has post-operatively changed position (e.g., extruded), one or more actions may be taken. In a simple case, an alert may be generated to a user indicating that further corrective action should be commenced. In another example, a change in position may result in the need for changes in the stimulation strategy that include, but are not limited to, deactivation of certain stimulation channels, change channel usage (i.e., from high to low frequency), etc. In a further example, detection of a post-operative position change may trigger safety mechanisms that disable the cochlear implant until, for example, the implant can be reprogrammed or, in extreme cases, the stimulating assembly can be properly repositioned. It is to be appreciated that these actions are merely illustrative and other actions are possible.

It is to be appreciated that the echo location techniques presented are useful not only in the post-operative environment of FIG. 5, but also during a cochlear implant insertion procedure. FIG. 6 is a block diagram of an arrangement that may be useful during implantation of a stimulating assembly. For ease of reference, the embodiment of FIG. 6 will be described with reference to the implantation of implantable component 544 of FIG. 5 into a recipient 655.

FIG. 6 illustrates a processing device 670 that is used to display an image (e.g., either a captured or reconstructed image) based on signals received from echo location devices 502 of stimulating assembly 518. Processing device 670 is a computing device that comprises a plurality of interfaces/ports 678(1)-678(N), a memory 680, a display device (e.g., screen) 682, a processor 684, and a user interface 686.

The interfaces 678(1)-678(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 6, 678(1) is connected to an external coil 630 and/or an external device (not shown) in communication with the external coil. Interface 678(1) may be configured to communicate with the external coil 630 (or other device) via a wired or wireless connection (e.g., telemetry, Bluetooth, etc.).

The memory 680 includes echo location logic 635 and imaging logic 694. In certain embodiments, the echo location logic 635 may operate similarly to echo location logic 525 of FIG. 5 to process echo location signals 560 from echo location devices 502. The imaging logic 694 may use data generated by the echo location logic 635 to reconstruct an image of the recipient's cochlea, as well as a representation of the stimulating assembly 518 within the cochlea, at display device 682.

Memory 680 may comprise read only memory (ROM), random access memory (RAM), magnetic disk storage media devices, optical storage media devices, flash memory devices, electrical, optical, or other physical/tangible memory storage devices. The processor 684 is, for example, a microprocessor or microcontroller that executes instructions for the echo location logic 635 and an imaging logic 694. Thus, in general, the memory 680 may comprise one or more tangible (non-transitory) computer readable storage media (e.g., a memory device) encoded with software comprising computer executable instructions and when the software is executed (by the processor 684) it is operable to perform the operations described herein in connection with echo location logic 635 and an imaging logic 694.

Figure 7:
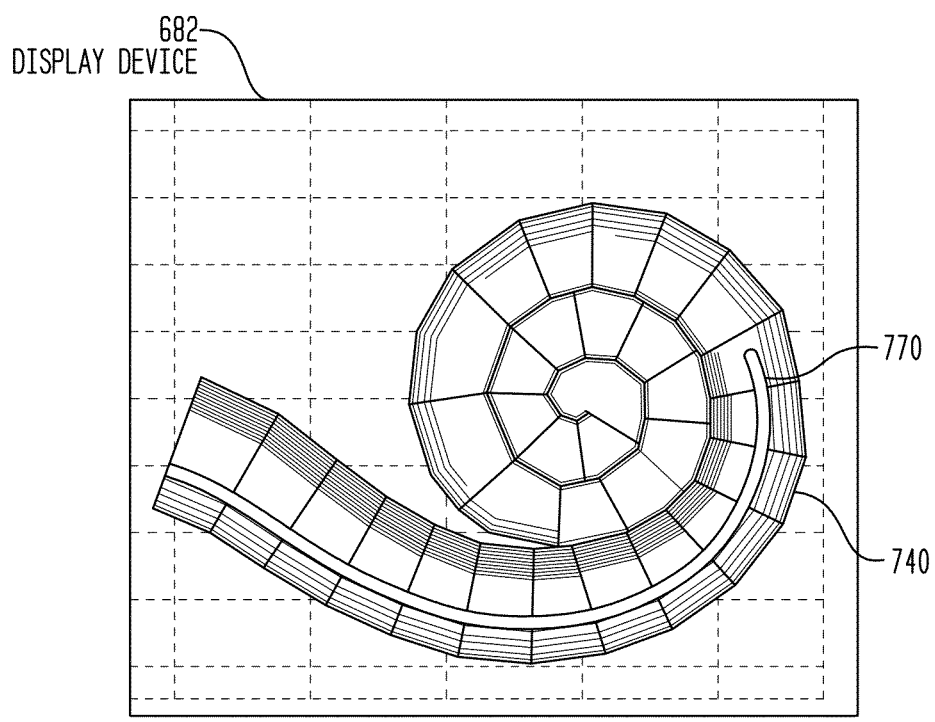
FIG. 7 is front view of a display screen configured to display a two-dimensional (2D) representation of a stimulating assembly and a cochlea in accordance with embodiments of the present invention.
Figure 8:
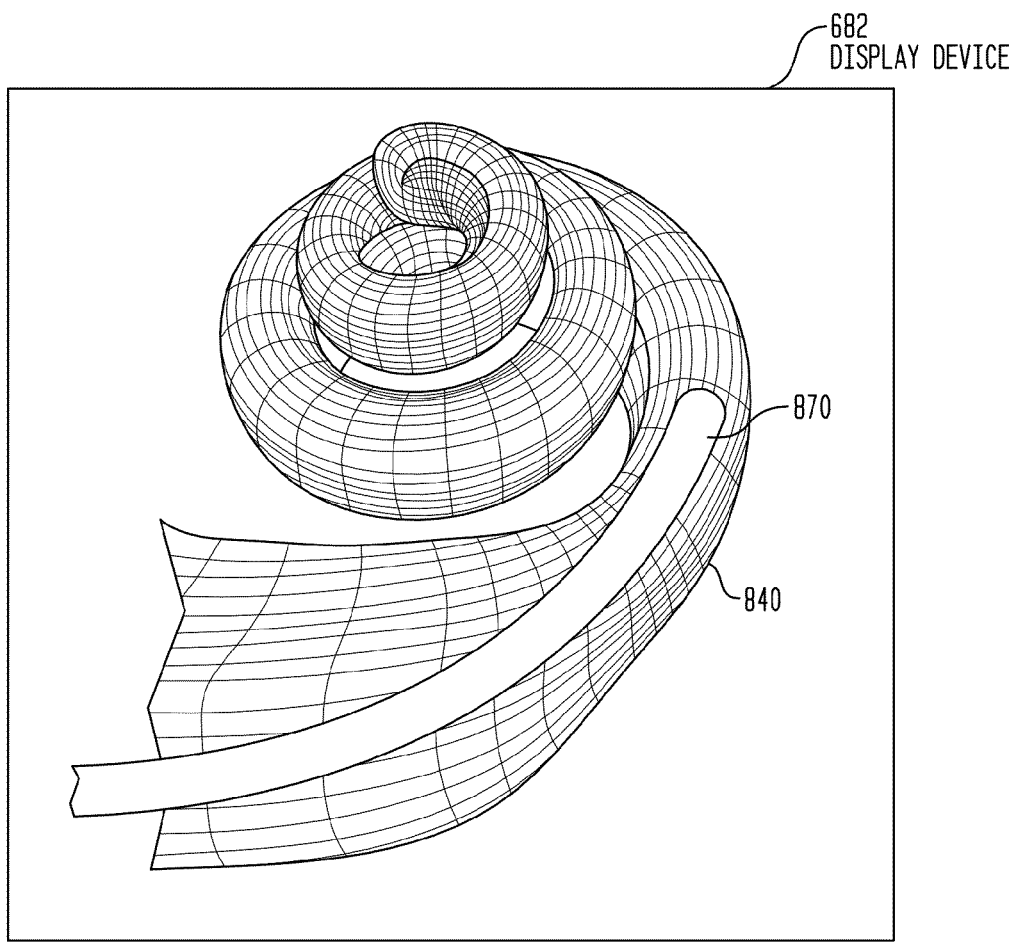
FIG. 8 is front view of a display screen configured to display a three-dimensional (3D) representation of a stimulating assembly and a cochlea in accordance with embodiments of the present invention.

FIGS. 7 and 8 are schematic diagrams illustrating example displays that may be generated by imaging logic 694 at display device 682. More specifically, FIG. 7 is a schematic diagram of illustrating an example in which display device 682 displays a two-dimensional representation 740 of a recipient's cochlea and a two-dimensional representation of 770 of stimulating assembly 518 during insertion therein. FIG. 8 is a schematic diagram illustrating an example in which display device 682 displays a three-dimensional representation 840 of a recipient's cochlea and a three-dimensional representation 870 of stimulating assembly 518 during insertion therein.

FIG. 6 illustrates a specific arrangement in which the processing device 670 enables the surgeon or other user to visualize the relative location of the stimulating assembly 518 within the cochlea during insertion. It is to be appreciated that the visual feedback is merely an illustrative use for the echo location signals 560 during insertion and that other uses are possible. For example, in other embodiments audible, haptic (tactile), or other types of feedback may be presented to the surgeon. For example, an audible warning may be generated if it is determined that an event has occurred or is about to occur (e.g., an audible warning may be generated when the tip of the stimulating assembly becomes stuck or has begun to contact or perforate the basilar membrane). Alternatively, vibrations or a buzzing may be generated if it is determined that an event has occurred or is about to occur. It is also to be appreciated that different types of feedback may be used in combination with one another (i.e., a visual presentation on a display screen along with an audible warning when an event has occurred or is about to occur).

As noted, FIG. 5 illustrates an arrangement in which the echo location techniques are partially executed within an external component of a cochlear implant, while FIG. 6 illustrates an arrangement in which the echo location techniques are partially executed at a computing device used during insertion surgery. It is to be appreciated that the echo location techniques may also be executed at other devices used with cochlear implants such as, for example, a remote control device.

Figure 9:
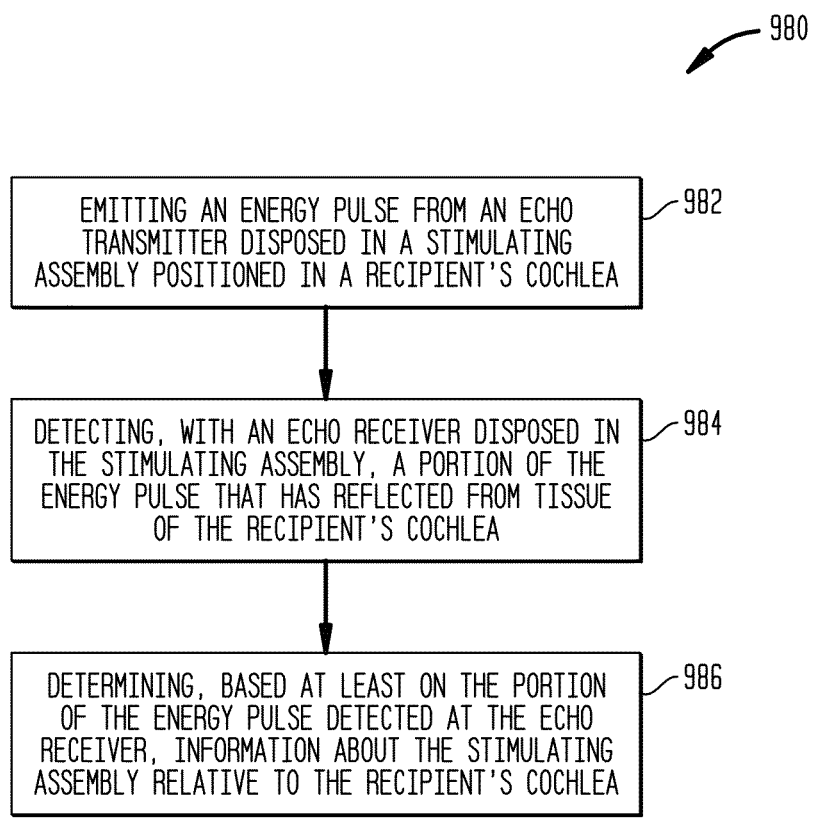
FIG. 9 is a flowchart of a method in accordance with embodiments presented herein.

FIG. 9 is a flowchart of an echo location method 980 in accordance with embodiments presented herein. Method 980 begins at 982 where an echo transmitter disposed in a stimulating assembly positioned within a recipient's cochlea emits an energy pulse (e.g., acoustic pulse, electromagnetic pulse, optical pulse, etc.). At 984, an echo receiver disposed in the stimulating assembly detects a portion of the energy pulse that has reflected from cochlea tissue. At 986, a processing device determines, based on information about the portion of the energy pulse detected at the echo receiver (i.e., based on the detected time, frequency, etc.), information about the stimulating assembly relative to the recipient's cochlea. The determined information may be, for example, the distance between a portion of the stimulation assembly and the recipient's cochlea tissue, the velocity/speed of insertion of the stimulating assembly, etc. In certain embodiments, the processing device may be configured to generate feedback to a user, as detailed above.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A cochlear implant comprising:
   an elongate stimulating assembly configured to be implanted in a recipient's cochlea;
   a transmitter disposed in the stimulating assembly configured to emit an energy pulse within the cochlea; and
   a receiver disposed in the stimulating assembly configured to detect at least a portion of the energy pulse reflected from tissue of the cochlea.

2. The cochlear implant of claim 1, wherein the receiver and transmitter provide signals to a processing device that is configured to determine a distance between the transmitter and the tissue of the cochlea.

3. The cochlear implant of claim 1, wherein the receiver and transmitter provide frequency signals to a processing device that is configured to determine a velocity of the stimulating assembly.

4. The cochlear implant of claim 1, further comprising a plurality of echo location pairs disposed in the stimulating assembly, wherein each echo location pair comprises a transmitter and a receiver.

5. The cochlear implant of claim 1, wherein the transmitter is configured to emit an acoustic energy pulse.

6. The cochlear implant of claim 1, wherein the transmitter is configured to emit an electromagnetic energy pulse.

7. The cochlear implant of claim 1, wherein the transmitter is configured to emit an optical energy pulse.

8. The cochlear implant of claim 1, further comprising a plurality of stimulating contacts disposed in the stimulating assembly.

9. The cochlear implant of claim 1, wherein the transmitter and receiver are parts of an integrated transceiver device.

10. A system, comprising:
    a processing device comprising:
       a memory,
       a processor
    an elongate stimulating assembly of a cochlear implant, in communication with location processing device, configured to be implanted in a recipient's cochlea and comprising:
       a transmitter configured to emit an energy pulse, and
       a receiver configured to detect at least a portion of the energy pulse reflected from the tissue,
       wherein one or more of the transmitter and the receiver send signals generated based on the emitted energy pulse and the detected portion of the emitted energy pulse to the processing device.

11. The system of claim 10, wherein the processing device is configured to process the signals to generate information about the stimulating assembly relative to the recipient's cochlea.

12. The system of claim 11, wherein the processing device is configured to determine a distance between the transmitter and the tissue of the cochlea.

13. The system of claim 10, wherein the processing device is configured to determine a velocity of the stimulating assembly.

14. The system of claim 11, wherein the processing device is configured to generate feedback to a user based on the processed signals.

15. The system of claim 10, wherein the transmitter is configured to emit an acoustic energy pulse.

16. The system of claim 10, wherein the transmitter is configured to emit an electromagnetic energy pulse.

17. The system of claim 10, wherein the transmitter is configured to emit an optical energy pulse.

18. The system of claim 10, wherein the processing device is an external component of the cochlear implant.

19. The system of claim 10, wherein the processing device is a separate computing device in communication with the stimulating assembly via a transcutaneous coil arrangement.

20. The system of claim 10, wherein the processing device is a remote control device operable with the cochlear implant.

21. A method comprising:
- emitting an energy pulse from a transmitter disposed in a stimulating assembly positioned in a recipient's cochlea;
- detecting, within a receiver of the location device, at least portion of the energy pulse reflected from tissue of the recipient; and
- determining, based at least on the portion of the energy pulse detected at the receiver, information about the stimulating assembly relative to the recipient's cochlea.

22. The method of claim 21, wherein determining information about the stimulating assembly relative to the recipient's cochlea comprises:
- determining a distance between the transmitter and the tissue of the cochlea.

23. The method of claim 21, wherein determining information about the stimulating assembly relative to the recipient's cochlea comprises:
- determining a velocity of the stimulating assembly.

24. The method of claim 21, wherein emitting the energy pulse from the transmitter comprises:
- emitting an acoustic energy pulse.

25. The method of claim 21, wherein emitting the energy pulse from the transmitter comprises:
- emitting an electromagnetic energy pulse.

26. The method of claim 21, wherein emitting the energy pulse from the transmitter comprises:
- emitting an optical energy pulse.

* * * * *